(12) United States Patent
Mathieu et al.

(10) Patent No.: US 7,232,464 B2
(45) Date of Patent: Jun. 19, 2007

(54) INTERVERTEBRAL IMPLANT

(75) Inventors: Claude Mathieu, Bettlach (CH); Christopher Marden John Cain, Norwood (AU)

(73) Assignee: Synthes (USA), West Chester, PA (US)

( * ) Notice: Subject to any disclaimer, the term of this patent is extended or adjusted under 35 U.S.C. 154(b) by 0 days.

(21) Appl. No.: 10/923,534

(22) Filed: Aug. 19, 2004

(65) Prior Publication Data
US 2005/0177236 A1    Aug. 11, 2005

Related U.S. Application Data

(63) Continuation of application No. PCT/CH02/00099, filed on Feb. 19, 2002.

(51) Int. Cl.
*A61F 2/44* (2006.01)

(52) U.S. Cl. ................................. 623/17.11

(58) Field of Classification Search .. 623/17.11–17.16; 606/61
See application file for complete search history.

(56) References Cited

U.S. PATENT DOCUMENTS

| | | |
|---|---|---|
| 2,621,145 A | 12/1952 | Sano |
| 4,135,506 A | 1/1979 | Ulrich |
| 4,501,269 A | 2/1985 | Bagby |
| 4,512,038 A | 4/1985 | Alexander et al. |
| 4,627,853 A | 12/1986 | Campbell et al. |
| 4,678,470 A | 7/1987 | Nashef et al. |
| 4,717,115 A | 1/1988 | Schmitz |
| 4,858,603 A | 8/1989 | Clemow et al. |
| 4,904,261 A * | 2/1990 | Dove et al. ............... 623/17.16 |
| 4,936,851 A | 6/1990 | Fox et al. |
| 4,950,296 A | 8/1990 | McIntyre |
| 4,961,740 A | 10/1990 | Ray et al. |
| 4,994,084 A | 2/1991 | Brennan |
| 5,026,373 A | 6/1991 | Ray et al. |
| 5,053,049 A | 10/1991 | Campbell |
| 5,062,850 A | 11/1991 | MacMillan et al. |
| 5,084,051 A | 1/1992 | Törmälä et al. |
| 5,112,354 A | 5/1992 | Sires |

(Continued)

FOREIGN PATENT DOCUMENTS

CA    2317791 A1    8/1999

(Continued)

*Primary Examiner*—Bruce Snow
(74) *Attorney, Agent, or Firm*—Stroock & Stroock & Lavan LLP

(57) ABSTRACT

The intervertebral implant is in the form of a three-dimensional structure (10) comprising (a) a top side (1) and an underside (2) which are designed to rest against the end plates of two adjacent vertebras, (b) a left side face (3) and a right side face (4), (c) a front face (5) and a rear face (6), (d) a horizontal center plane situated between the top side (1) and the underside (2), (e) a vertical center plane (8) situated between the left side face (3) and the right side face (8) and (f) a plurality of boreholes (9) passing through the implant structure (10) that are designed to receive longitudinal affixation elements (20), the axes (19) of said elements intersecting the horizontal center plane (7). At least one of the boreholes (9) is designed in a manner that the affixation element (10) received in it can be rigidly connected to the intervertebral implant. Said connection is implemented using a thread or by matching conical surfaces.

32 Claims, 3 Drawing Sheets

U.S. PATENT DOCUMENTS

| | | |
|---|---|---|
| 5,192,327 A | 3/1993 | Brantigan |
| 5,211,664 A | 5/1993 | Tepic et al. |
| 5,281,226 A | 1/1994 | Davydov et al. |
| 5,284,655 A | 2/1994 | Bogdansky et al. |
| 5,298,254 A | 3/1994 | Prewett et al. |
| 5,314,476 A | 5/1994 | Prewett et al. |
| 5,348,788 A | 9/1994 | White |
| 5,405,391 A | 4/1995 | Hednerson et al. |
| 5,423,817 A | 6/1995 | Lin |
| 5,439,684 A | 8/1995 | Prewett et al. |
| 5,458,638 A | 10/1995 | Kuslich et al. |
| 5,489,308 A | 2/1996 | Kuslich et al. |
| 5,507,818 A | 4/1996 | McLaughlin |
| 5,514,180 A | 5/1996 | Heggeness et al. |
| 5,522,899 A | 6/1996 | Michelson |
| 5,534,030 A | 7/1996 | Navarro et al. |
| 5,549,679 A | 8/1996 | Kuslich |
| 5,554,191 A | 9/1996 | Lahille et al. |
| 5,556,430 A | 9/1996 | Gendler |
| 5,569,308 A | 10/1996 | Sottosanti |
| 5,571,190 A | 11/1996 | Ulrich et al. |
| 5,571,192 A | 11/1996 | Schönhöffer |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,676,699 A | 10/1997 | Gogolewski |
| 5,683,394 A | 11/1997 | Rinner |
| 5,683,463 A | 11/1997 | Godefroy et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,728,159 A | 3/1998 | Stroever et al. |
| 5,735,905 A | 4/1998 | Parr |
| 5,766,253 A | 6/1998 | Brosnahan, III |
| 5,776,194 A | 7/1998 | Mikol et al. |
| 5,776,197 A | 7/1998 | Rabbe et al. |
| 5,776,198 A | 7/1998 | Rabbe et al. |
| 5,776,199 A | 7/1998 | Michelson |
| 5,782,915 A | 7/1998 | Stone |
| 5,785,710 A | 7/1998 | Michelson |
| 5,865,849 A | 2/1999 | Stone |
| 5,876,452 A | 3/1999 | Athanasiou et al. |
| 5,885,299 A | 3/1999 | Winslow et al. |
| 5,888,222 A | 3/1999 | Coates et al. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,338 A | 5/1999 | Stone |
| 5,904,719 A | 5/1999 | Errico et al. |
| 5,910,315 A | 6/1999 | Stevenson et al. |
| 5,922,027 A | 7/1999 | Stone |
| 5,944,755 A | 8/1999 | Stone |
| 5,968,098 A | 10/1999 | Winslow |
| 5,972,368 A | 10/1999 | McKay |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,013,853 A | 1/2000 | Athanasiou et al. |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,080,158 A | 6/2000 | Lin |
| 6,080,193 A | 6/2000 | Hochshuler et al. |
| 6,090,998 A | 7/2000 | Grooms et al. |
| 6,096,081 A | 8/2000 | Grivas et al. |
| 6,110,482 A | 8/2000 | Khouri et al. |
| 6,123,731 A | 9/2000 | Boyce et al. |
| 6,129,763 A | 10/2000 | Chauvin et al. |
| 6,143,030 A | 11/2000 | Schroder |
| 6,143,033 A | 11/2000 | Paul et al. |
| 6,156,070 A | 12/2000 | Incavo et al. |
| 6,193,756 B1 | 2/2001 | Studer et al. |
| 6,200,347 B1 | 3/2001 | Anderson et al. |
| 6,206,922 B1 | 3/2001 | Zdeblick et al. |
| 6,231,610 B1 | 5/2001 | Geisler |
| 6,235,059 B1 | 5/2001 | Benezech et al. |
| 6,241,769 B1 | 6/2001 | Nicholson et al. |
| 6,245,108 B1 | 6/2001 | Biscup |
| 6,258,125 B1 | 7/2001 | Paul et al. |
| 6,261,586 B1 | 7/2001 | McKay |
| 6,264,695 B1 | 7/2001 | Stoy |
| 6,270,528 B1 | 8/2001 | McKay |
| 6,342,074 B1 * | 1/2002 | Simpson ............... 623/17.11 |
| 6,364,880 B1 | 4/2002 | Michelson |
| 6,423,063 B1 | 7/2002 | Bonutti |
| 6,458,158 B1 | 10/2002 | Anderson et al. |
| 6,468,311 B2 | 10/2002 | Boyd et al. |
| 6,569,201 B2 | 5/2003 | Moumene et al. |
| 6,638,310 B2 | 10/2003 | Lin et al. |
| 6,761,739 B2 | 7/2004 | Shepard |
| 6,984,234 B2 | 1/2006 | Bray |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2002/0010511 A1 | 1/2002 | Michelson |
| 2002/0029084 A1 | 3/2002 | Paul et al. |
| 2002/0082597 A1 * | 6/2002 | Fraser .................... 606/61 |
| 2002/0091447 A1 | 7/2002 | Shimp et al. |
| 2002/0106393 A1 | 8/2002 | Bianchi et al. |
| 2002/0111680 A1 | 8/2002 | Michelson |
| 2003/0125739 A1 | 7/2003 | Bagga et al. |
| 2004/0210314 A1 * | 10/2004 | Michelson ............ 623/17.16 |
| 2005/0033433 A1 * | 2/2005 | Michelson ............ 623/17.11 |

FOREIGN PATENT DOCUMENTS

| | | |
|---|---|---|
| DE | 30 42 003 A1 | 7/1982 |
| DE | 39 33 459 A1 | 4/1991 |
| DE | 42 42 889 A1 | 6/1994 |
| DE | 44 09 392 A1 | 9/1995 |
| DE | 44 23 257 A1 | 1/1996 |
| DE | 195 04 867 C1 | 2/1996 |
| DE | 299 13 200 U1 | 9/1999 |
| EP | 0505634 A1 | 9/1992 |
| EP | 0517030 A2 | 12/1992 |
| EP | 0517030 A3 | 4/1993 |
| EP | 0577178 A1 | 1/1994 |
| EP | 0639351 A2 | 2/1995 |
| EP | 0639351 A3 | 3/1995 |
| EP | 0517030 B1 | 9/1996 |
| EP | 0505634 B1 | 8/1997 |
| EP | 0966930 | 12/1999 |
| EP | 0968692 A1 | 1/2000 |
| EP | 0906065 B1 | 1/2004 |
| EP | 1051133 B1 | 10/2004 |
| FR | 2 552 659 | 4/1985 |
| FR | 2 697 996 | 5/1994 |
| FR | 2 700 947 | 8/1994 |
| FR | 2 753 368 | 3/1998 |
| GB | 2 148 122 A | 5/1985 |
| SU | 1465040 A1 | 3/1989 |
| WO | WO 88/03417 | 5/1988 |

| | | | | | | |
|---|---|---|---|---|---|---|
| WO | WO 88/10100 | 12/1988 | | WO | WO 00/07527 | 2/2000 |
| WO | WO 92/01428 | 2/1992 | | WO | WO 00/07528 | 2/2000 |
| WO | WO 95/21053 | 8/1995 | | WO | WO 00/30568 | 6/2000 |
| WO | WO 96/39988 | 12/1996 | | WO | WO 00/40177 | 7/2000 |
| WO | WO 97/20526 | 6/1997 | | WO | WO 00/41654 A2 | 7/2000 |
| WO | WO 97/25941 | 7/1997 | | WO | WO 00/41654 A3 | 7/2000 |
| WO | WO 97/25945 | 7/1997 | | WO | WO 00/59412 | 10/2000 |
| WO | WO 97/39693 A1 | 10/1997 | | WO | WO 00/66044 A1 | 11/2000 |
| WO | WO 98/17209 | 4/1998 | | WO | WO 00/66045 A | 11/2000 |
| WO | WO 98/55052 | 12/1998 | | WO | WO 00/66045 A1 | 11/2000 |
| WO | WO 98/56319 | 12/1998 | | WO | WO 00/74607 A1 | 12/2000 |
| WO | WO 98/56433 | 12/1998 | | WO | WO 01/56497 A2 | 8/2001 |
| WO | WO 99/29271 | 6/1999 | | WO | WO 01/56497 A3 | 8/2001 |
| WO | WO 99/32055 | 7/1999 | | WO | WO 01/93742 A2 | 12/2001 |
| WO | WO 99/38461 | 8/1999 | | WO | WO 01/93742 A3 | 12/2001 |
| WO | WO 99/38463 | 8/1999 | | WO | WO 01/95837 A1 | 12/2001 |
| WO | WO 99/38463 A2 | 8/1999 | | | | |
| WO | WO 99/38463 A3 | 8/1999 | | | | |
| WO | WO 99/56675 | 11/1999 | | | | |

\* cited by examiner

INTERVERTEBRAL IMPLANT

CROSS-REFERENCE TO RELATED APPLICATIONS

This is a continuation of International Application No. PCT/CH02/00099, filed Feb. 19, 2002, the entirety of which is expressly incorporated by reference herein.

FIELD OF THE INVENTION

The present invention relates to an intervertebral implant.

BACKGROUND OF THE INVENTION

Such an intervertebral implant is known from the British patent document 2,207,607 A which discloses a horseshoe implant structure having a plurality of cylindrical holes. These holes are fitted with inner, smooth surfaces and comprise only one stop for the heads of the bone screws to be inserted into them. This design incurs the drawback that the inserted affixation screws may be anchored into the bone only by their shanks, a rigid connection with the horseshoe shaped intervertebral implant being lacking. As soon as the anchoring of the bone screw in the bone is weakened, the intervertebral implant becomes displaceable relative to the screw and the bone screws may then migrate while endangering the blood vessels. Moreover the loosening of the intervertebral implant may entail pseudoarthrosis.

The above cited state of the art is intended merely to elucidate the background of the present invention but it does imply that the cited state of the art had actually been made public or was publicly known at the time of this application or at the time of its priority.

SUMMARY OF THE INVENTION

The objective of the present invention is palliation. This invention creates an intervertebral implant which is able to rigidly connect to bone affixation means in a manner that even in the event of bone structure weakening, loosening between the intervertebral implant and the bone affixation means shall be precluded.

The above problem is solved in the present invention by an intervertebral implant exhibiting the features of claim 1.

The advantages offered by the present invention substantially are attained by the rigid, that is by the firm connection between the intervertebral implant and the longitudinal affixing elements. Basically two different embodiment modes are available to attain said rigid connection.

In a first embodiment mode, at least one of the boreholes shall be internally threaded. In this case a matching bone screw fitted with a thread head may be rigidly screwed into the implant.

As regards a second embodiment mode, a front plate is mounted at the front surface of the three dimensional (3D) implant structure so as to be configured vertically to the horizontal center plane of the intervertebral implant, said boreholes passing through said front plate and receiving the anchored longitudinal affixation elements. Compared to the state of the art of a two-part implant, wherein a front plate is implanted in a separate operational step, the above design of the present invention offers the advantage that the intervertebral implant shall be implanted in a single step and hence in a simple and quicker manner. The invention offers a further advantage in that the intervertebral implant shall be affixed as frontally to the vertebra as possible, namely at a place where good bone material may be expected to be. As a result anterior displacement is restricted without thereby incurring greater danger to the surrounding structures than when using a state of the art intervertebral implant. The load still is being borne by the compressed vertebral implant, not by the front plate or the affixation screws.

In yet another embodiment mode of the present invention, the front plate is displaceably configured in the 3D implant structure in order that it may move vertically relative to this 3D implant structure. "Stress shielding" is attained in this manner (namely protection from or neutralization of mechanical stresses), and as a result the end plates may gradually match the intervertebral implant during the healing process.

As regards a further embodiment, the front plate is made of a material different from that of the 3D implant structure.

As regards a further embodiment of the present invention, at least one borehole tapers conically towards its underside and as a result a bone screw fitted with a matching conical head may be rigidly anchored in said borehole. Preferably the conical borehole exhibits a cone angle smaller than the resultant angle of friction. Appropriately the borehole's conicity shall be 1:3.75 to 1:20, preferably 1:5 to 1:15.

As regards a further embodiment mode of the present invention, the intervertebral implant side faces shall all be substantially convex.

Appropriately the intervertebral implant's top and/or undersides are not planar but convex. In this manner better matching to the end plates of the adjacent vertebras may be attained.

The boreholes preferably shall not pass through the left and right intervertebral implant side faces. Preferably again no borehole shall run through the rear surface.

As regards a further preferred embodiment mode of the present invention, at least two boreholes shall be mutually parallel. This features facilitates inserting the vertebral implant during implantation.

As regards another preferred embodiment mode of the present invention, at least two boreholes shall run in mutually divergent manner as seen from the front side. As a result the bone screws shall move into a vertebral region offering better bone quality than found at the vertebra's center. Appropriately the borehole axes subtend an angle of 25° to 70°, preferably 35° to 55° with the horizontal center plane. This feature offers improved access for screw insertion.

As regards a further embodiment mode of the present invention, the boreholes shall not cross the horizontal center plane.

Depending on circumstance, two, three, four or even more longitudinal affixation elements may rigidly connected to the intervertebral implant; appropriately at least one affixation element shall pass through the top side and at least one affixation element shall pass through the intervertebral implant side.

Preferably the longitudinal affixation elements shall be bone screws comprising a head and a shank, said head preferably being fitted with an external thread that matches the inner thread of the intervertebral implant's borehole. As regards a second appropriate connection, preferably a bone screw shall be used of which the head tapers conically in the direction of the shank, the head's conicity corresponding to that of the intervertebral implant's borehole.

Regarding a further embodiment mode, at least two longitudinal affixation elements pass through the top side and at least two longitudinal affixation elements pass through the underside. In this manner the intervertebral implant is optimally anchored into the adjacent vertebras.

Preferably the screw-shaped longitudinal affixation elements exhibit a self-boring and self-tapping external thread. The longitudinal affixation elements also may be designed as unthreaded cylindrical pins fitted with a boring tip, preferably in the form of a trocar.

In another embodiment variation, the longitudinal affixation elements are spiral springs; lastly said longitudinal affixation elements also may be designed as single or multi-wing spiral blades.

In a further embodiment mode of the present invention, the longitudinal affixation element tip may be anchored in the structure of the intervertebral implant, as a result of which the head of the longitudinal affixation element may be anchored in the adjacent vertebra.

In a further embodiment mode of the present invention, the longitudinal affixation element head exhibits a widened diameter; also a support disk is provided for said head to rest against the vertebra.

The intervertebral implant may be made of any physiologically compatible material, though appropriately the implant structure shall consist of a physiologically compatible plastic, preferably an unreinforced plastic. The advantage offered by the invention over the already known, fiber-reinforced plastics used in implantology is that no reinforcing fibers will be bared—an eventuality that would be clinically disadvantageous. Appropriately bone screws consisting of non-reinforced plastic of which the external threads exhibit load bevels of 11° to 14°, preferably 12° to 13°, may be used in such an implant structure. The relatively small slope of the load bevel implements high clamping forces, as a result of which radial elongation and danger of cracking of the plastic are reduced. Appropriately the bone screws' external thread exhibits the bones at an angular pitch of 6° to 10°, preferably 7° to 9°. This particular angular pitch produces thread self-locking and prevents the bone screw from loosening on its own.

The borehole may be in the form of a metal bush fitted with an inner thread for the purpose of improving anchoring the bone screw in the plastic implant structure. The intervertebral implant also may consist partly of plastic and, in the borehole zones, of metal. This design offers improved guidance and anchoring of the bone screw in the intervertebral implant.

As regards a further preferred embodiment mode, the inside borehole walls are smooth, the thread head of a metallic, longitudinal affixation element cutting or tapping into said smooth wall.

BRIEF DESCRIPTION OF THE DRAWINGS

The present invention and further embodiment modes of it are elucidated below in relation to the partly schematic representation of two illustrative embodiments.

DETAILED DESCRIPTION OF THE INVENTION

Figure 1:
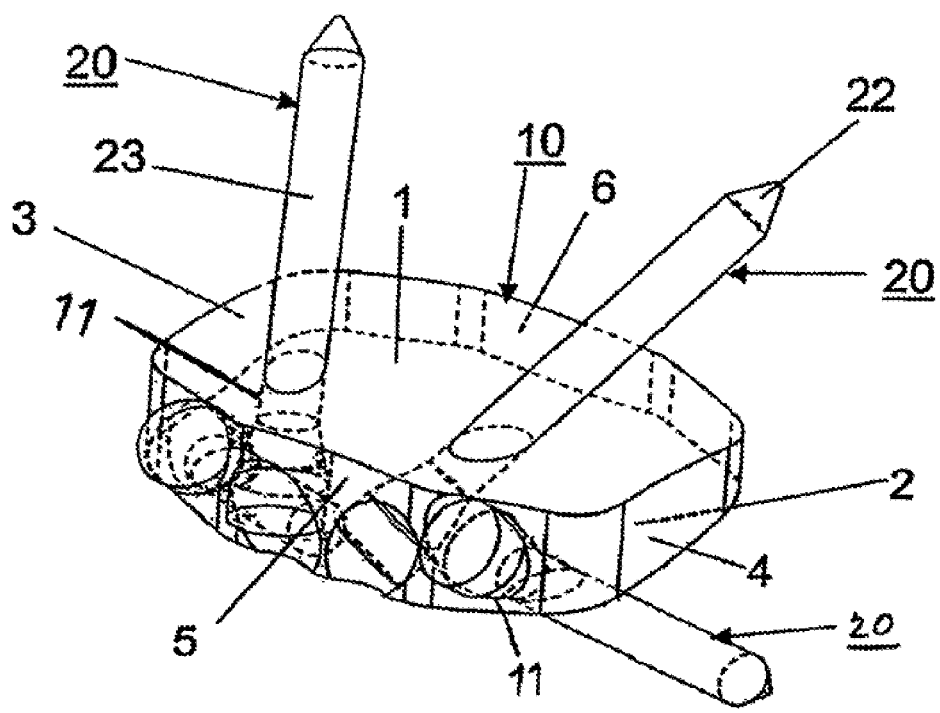
FIG. 1 is a perspective view including a partial section of the intervertebral implant with inserted bone screws.
Figure 2:
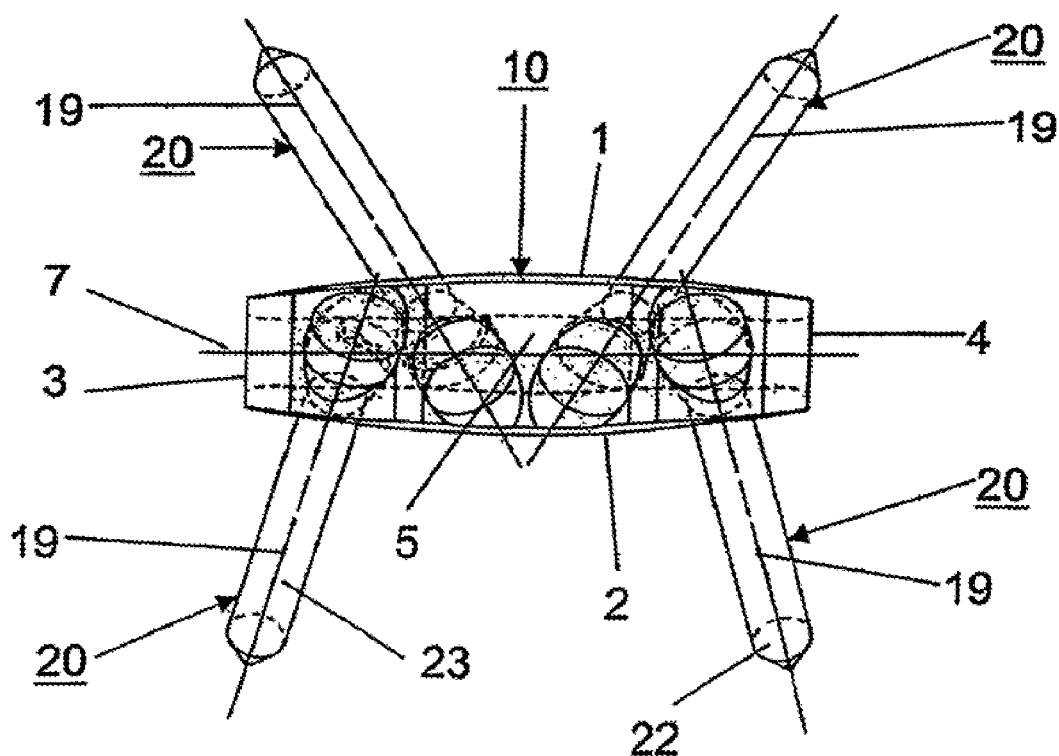
FIG. 2 is a front view of the intervertebral implant of FIG. 1.
Figure 3:
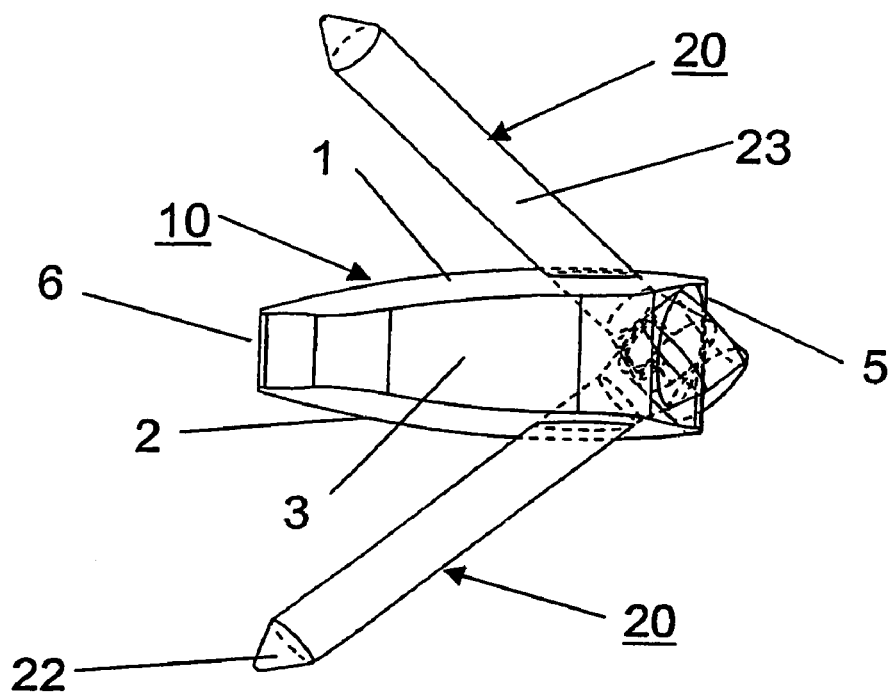
FIG. 3 is a sideview of the intervertebral implant of FIG. 1.
Figure 4:
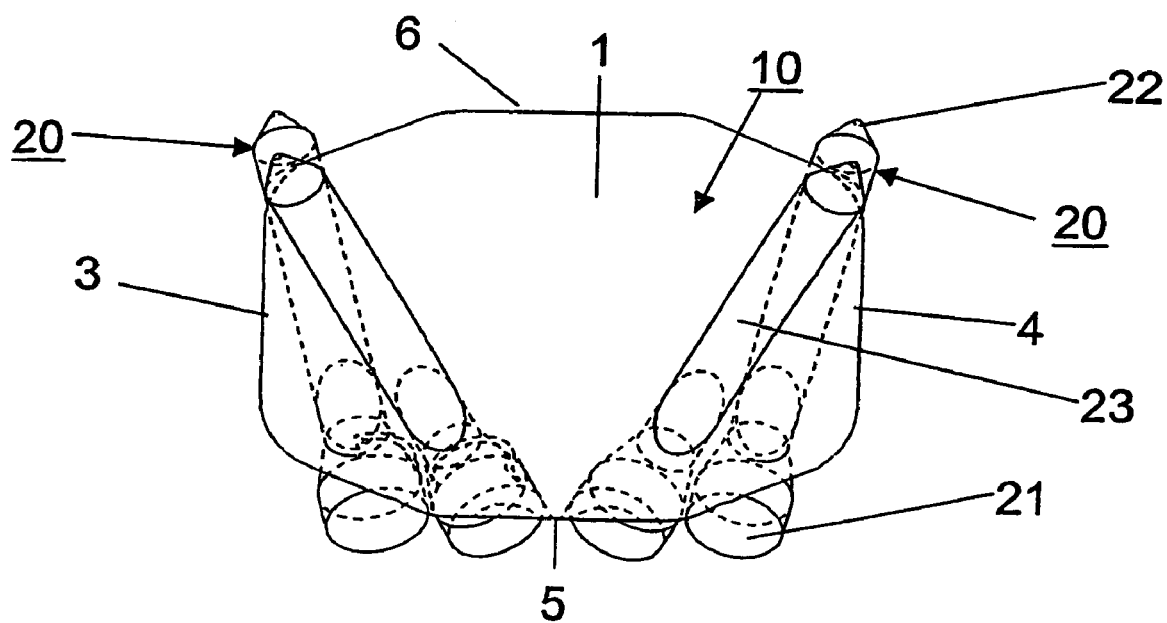
FIG. 4 is a topview of the intervertebral implant of FIG. 1.

The intervertebral implant of FIGS. 1 through 4 consists of a 3D structure 10 exhibiting both a convex top side 1 and a convex underside 2, the two sides each being designed to rest against the end plates of two adjacent vertebras. To attain improved anchoring, the top side 1 and the underside 2 may be topographically shaped and be fitted with grooves, ribs or teeth, or their surfaces may be merely roughened.

The 3D implant structure 10 moreover comprises a left side face 3 and a right side face 4, also a front face 5 and a rear face 6. The implant structure 10 also may be hollow and its outer surface may comprise perforations.

The implant structure 10 comprises a plurality of boreholes 9 passing through it and receiving longitudinal affixation elements 20. Preferably four such boreholes 9 shall be provided.

At least one of the boreholes 9 is designed in a way that the longitudinal affixation element 20 received therein may be rigidly connected to the intervertebral implant. The boreholes 9 are conical for that purpose.

Preferably the affixation elements 20 are bone screws having a head 21 and a tip 22. The head 21 conically tapers toward the shank 23, the conicity of the head 21 corresponding to the conicity of the borehole 9. Moreover the four boreholes 9 may be fitted with inner threads 11.

Figure 5:
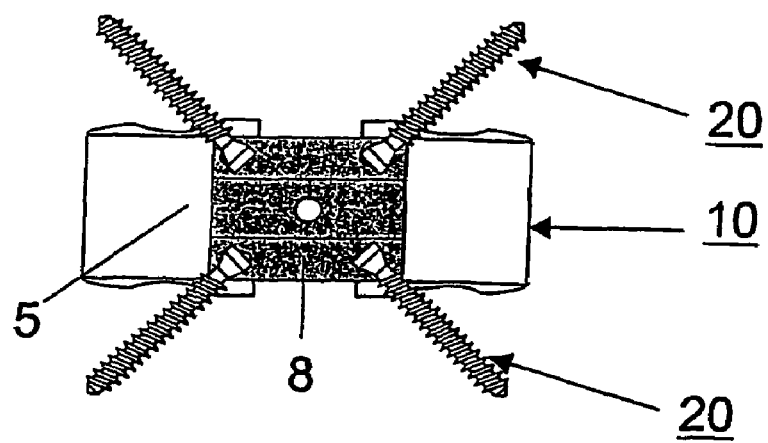
FIG. 5 is a front view of the intervertebral implant with a front insert, in partial section.
Figure 6:
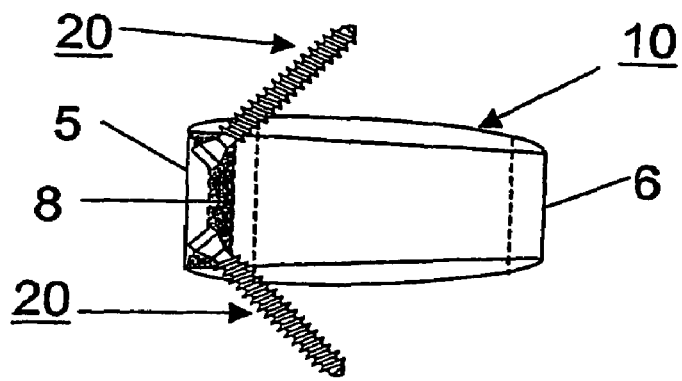
FIG. 6 is a vertical, longitudinal section of the intervertebral implant of FIG. 5.
Figure 7:
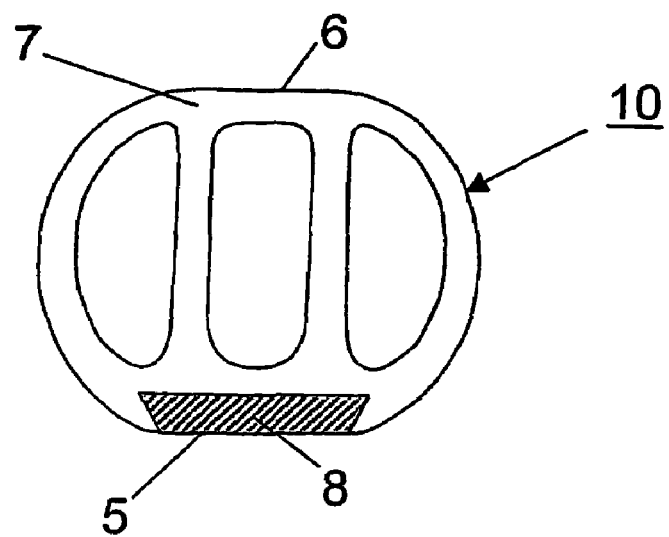
FIG. 7 is a horizontal cross-section of the intervertebral implant of FIG. 5.

As regards the embodiment variation shown in FIGS. 5 through 7, the 3D structure 10 is fitted at its front face 5 with a preferably metallic insert 8 into which the affixation elements 20 may be anchored. The insert 8 is mounted in vertically displaceable manner in the 3D structure 10.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed:

1. An intervertebral implant comprising:
   a body having an upper surface at least partially configured to lie adjacent to the endplate of a first vertebrae and defining an upper plane, and a lower surface at least partially configured to lie adjacent to the endplate of a second vertebrae and defining a lower plane;
   a plate displaceably associated with the body, and having a first fastener hole for receiving a first fastener insertable into the first vertebrae, and a second fastener hole for receiving a second fastener insertable into the second vertebrae;
   wherein at least a portion of the plate is inset in the body;
   wherein first and second fasteners each have a head, the heads of the fasteners are retained between the upper and lower planes.

2. The implant of claim 1, wherein the first fastener is configured to be divergent the second fastener.

3. The implant of claim 1, wherein the first fastener hole is threaded.

4. The implant of claim 1, wherein the plate has a plurality of fastener holes located along its periphery.

5. The implant of claim 1, wherein at least one of the upper surface and the lower surface includes teeth.

6. The implant of claim 1, wherein a surface of the plate is substantially flush with the a surface of the body.

7. The implant of claim 1, wherein the body comprises a horizontal center plane, and wherein the plate is disposed substantially perpendicular to the horizontal center plane.

8. The implant of claim 1, wherein the body comprises a horizontal center plane, and wherein the plate is displaceable in a direction substantially perpendicular to the horizontal center plane.

9. The implant of claim 1, wherein the plate is comprised of a first material, and wherein the body is comprised of a second material different than the first material.

10. The implant of claim 1, wherein the plate is comprised of metal.

11. The implant of claim 1, wherein the body is comprised of plastic.

12. The implant of claim 1, wherein the body further comprises a convex side surface.

13. The implant of claim 1, wherein at least one of the upper surface and lower surface is convex.

14. The implant of claim 1, wherein the body comprises a horizontal center plane, and wherein the plate has a fastener hole having an axis angled from about 25 degrees to about 70 degrees with respect to the horizontal center plane.

15. The implant of claim 14, wherein the axis is angled from about 35 degrees to about 50 degrees with respect to the horizontal center plane.

16. The implant of claim 1, wherein the plate is allowed to translate to promote healing.

17. The implant of claim 1, wherein the plate is allowed to translate to neutralize mechanical stresses.

18. An intervertebral implant comprising:
   an upper surface at least partially to lie configured to lie adjacent to the endplate of a first vertebrae, and defining an upper plane;
   a lower surface at least partially configured to lie adjacent to the endplate of a second vertebrae, and defining a lower plane;
   at least a first opening and a second opening, wherein the first and second openings extend from the lower surface through to the upper surface;
   a front surface having a recess; and
   a plate at least partially disposed in the recess, and having inn a first fastener hole for receiving a first insertable into the first vertebrae, and a second fastener hole for receiving a second fastener insertable into the second vertebrae;
   wherein first and second fasteners each have a head, the heads of the fasteners are
   retained between the upper and lower planes.

19. The implant of claim 18, wherein the first fastener is configured to be divergent the second fastener.

20. The implant of claim 18, wherein the first fastener hole is threaded.

21. The implant of claim 18, wherein the plate has a plurality of fastener holes located along its periphery.

22. The implant of claim 18, wherein, at least one of the upper surface and the lower surface includes teeth.

23. The implant if claim 18, wherein the plate is displaceably associated with the front surface.

24. The implant of claim 18, further comprising a horizontal center plane, and wherein the plate is disposed substantially perpendicular to the horizontal center plane.

25. The implant of claim 18, further comprising a horizontal center plane, and wherein the plate is displaceable in a direction substantially perpendicular to the horizontal center plane.

26. The implant of claim 18, wherein the plate is comprised of a first material, and wherein the remainder of the implant is comprised of a second material different than the first material.

27. The implant of claim 18, wherein the plate is comprised of metal.

28. The implant of claim 18, wherein at least a portion of the implant is comprised of plastic.

29. The implant of claim 18, further comprising a convex side surface.

30. The implant of claim 18, wherein at least one of the upper surface and lower surface is convex.

31. The implant of claim 18, further comprising a horizontal center lane, and wherein the plate has a fastener hole having an axis angled from about 25 degrees to about 70 degrees with respect to the horizontal center plane.

32. The implant of claim 31, wherein the axis is angled from about 35 degrees to about 50 degrees wills respect to the horizontal center plane.

* * * * *

UNITED STATES PATENT AND TRADEMARK OFFICE
CERTIFICATE OF CORRECTION

PATENT NO. : 7,232,464 B2  Page 1 of 1
APPLICATION NO. : 10/923534
DATED : June 19, 2007
INVENTOR(S) : Claude Mathieu et al.

It is certified that error appears in the above-identified patent and that said Letters Patent is hereby corrected as shown below:

Column 5, line 6 reads -- is substantially flush with the a surface of the body -- should read
-- is substantially flush with the surface of the body --.

Column 5, line 39 reads -- an upper surface at least partially to lie configured to lie -- should read
-- an upper surface at least partially configured to lie --.

Column 6, line 3 reads -- inn a first fastener hole for receiving a first insertable -- should read
-- a first fastener hole for receiving a first fastener insertable --.

Column 6, line 40 reads -- horizontal center lane, and wherein the plate has a fasterner hole -- should read
-- horizontal center plane, and wherein the plate has a fasterner hole --.

Signed and Sealed this

Fifth Day of January, 2010

David J. Kappos
*Director of the United States Patent and Trademark Office*